(12) United States Patent
Parthasarathy et al.

(10) Patent No.: US 10,251,627 B2
(45) Date of Patent: Apr. 9, 2019

(54) ELASTOGRAPHY MEASUREMENT SYSTEM AND METHOD

(71) Applicant: KONINKLIJKE PHILIPS N.V., Eindhoven (NL)

(72) Inventors: Vijay Parthasarathy, Mt. Kisco, NY (US); Hua Xie, Ossining, NY (US); Jean-luc Robert, White Plains, NY (US); Shiwei Zhou, Yorktown Heights, NY (US); Vijay Thakur Shamdasani, Kenmore, WA (US)

(73) Assignee: KONINKLIJKE PHILIPS N. V., Eindhoven (NL)

( * ) Notice: Subject to any disclaimer, the term of this patent is extended or adjusted under 35 U.S.C. 154(b) by 376 days.

(21) Appl. No.: 14/900,199

(22) PCT Filed: Jun. 25, 2014

(86) PCT No.: PCT/IB2014/062582
§ 371 (c)(1),
(2) Date: Dec. 21, 2015

(87) PCT Pub. No.: WO2014/207668
PCT Pub. Date: Dec. 31, 2014

(65) Prior Publication Data
US 2016/0143621 A1 May 26, 2016

Related U.S. Application Data

(60) Provisional application No. 61/839,653, filed on Jun. 26, 2013.

(51) Int. Cl.
*A61B 8/00* (2006.01)
*A61B 8/08* (2006.01)
(Continued)

(52) U.S. Cl.
CPC .............. *A61B 8/469* (2013.01); *A61B 8/085* (2013.01); *A61B 8/4245* (2013.01);
(Continued)

(58) Field of Classification Search
CPC .......... A61B 8/469; A61B 8/485; A61B 8/483
See application file for complete search history.

(56) References Cited

U.S. PATENT DOCUMENTS 7,223,241 B2   5/2007   Radulescu
2004/0254460 A1*  12/2004  Burcher ............... A61B 5/6843
                                                         600/437
(Continued)

FOREIGN PATENT DOCUMENTS

JP   WO 2012105152 A1 *  8/2012  ............... A61B 8/42
WO   WO 2013026141 A1 *  2/2013  ............. A61B 8/485

OTHER PUBLICATIONS

E. Fiorini "Real Time Elastography as a Noninvasive Technique for Quantification of Fibrosis in Patients With Chronic Viral Liver Disease" Journal of Ultrasound (2012) vol. 15, p. 220-225.

*Primary Examiner* — Joseph M Santos Rodriguez

(57) ABSTRACT

The present invention relates to an ultrasound elastography system (10) for providing an elastography measurement result of an anatomical site (32) a corresponding method. The system (10) is configured to visualize a suitability for shear wave elastography of the region of interest (33) to the user within the ultrasound image (52) and/or to recommend an elastography acquisition plane (48, 50) for conducting shear wave elastography to the user. By this, proper selection of a location for an elastography measurement may be supported.

15 Claims, 11 Drawing Sheets

(51) Int. Cl.
*G01S 7/52* (2006.01)
*G01S 15/89* (2006.01)

(52) U.S. Cl.
CPC ............ *A61B 8/4263* (2013.01); *A61B 8/483* (2013.01); *A61B 8/485* (2013.01); *G01S 7/52036* (2013.01); *G01S 7/52042* (2013.01); *A61B 8/5207* (2013.01); *G01S 15/8915* (2013.01); *G01S 15/8925* (2013.01)

(56) References Cited

U.S. PATENT DOCUMENTS

| | | | |
|---|---|---|---|
| 2011/0066030 A1 | 3/2011 | Yao | |
| 2012/0128223 A1 | 5/2012 | Rivaz et al. | |
| 2012/0130227 A1* | 5/2012 | McGee | A61B 5/055 600/411 |
| 2013/0317361 A1* | 11/2013 | Tabaru | A61B 8/42 600/438 |
| 2013/0317371 A1 | 11/2013 | Takei | |
| 2014/0330122 A1* | 11/2014 | Baghani | A61B 8/485 600/438 |

\* cited by examiner

ELASTOGRAPHY MEASUREMENT SYSTEM AND METHOD

This application is the U.S. National Phase application under 35 U.S.C. § 371 of International Application No. PCT/IB2014/060079, filed on Mar. 24, 2014, which claims the benefit of U.S. Application No. 61/804,783 filed on Mar. 25, 2013. These applications are hereby incorporated by reference herein.

FIELD OF THE INVENTION

The present invention relates to an ultrasound elastography system for providing an elastography measurement result of an anatomical site and an ultrasound elastography method for inspecting an anatomical site with an ultrasound elastography system. The present invention further relates to a computer program for implementing such method.

BACKGROUND OF THE INVENTION

Limitations of liver biopsy have led to the development of various non-invasive evaluations of liver fibrosis that are more suitable for screening, treatment monitoring, and follow-up. Ultrasound shear wave elastography technique is known as technique for non-invasive liver fibrosis staging due to its absolute stiffness quantification capability, real-time, cost-efficient and portable features. Commercial products are already available, for example the Philips Ultrasound new release shear wave Elastography Point Quantification (ElastPQ). With such a method, acoustic radiation force is used to stress the liver or any other anatomical site mechanically and produce a shear wave. The resulting tissue displacement is measured and used to estimate the elasticity of the anatomical site, which for example has been found to correlate with fibrosis stage in the case of a liver being the anatomical site.

Due to system limitations such as transducer heating and physical limitations such as shear wave fast attenuation, current commercial shear wave elastography products usually only provide measurement at a user selected point location or a bigger region of interest (ROI) spatially confined within the B-mode field of view. In a typical workflow, the user selects a suspicious region under the conventional ultrasound B-mode imaging, activates shear wave elastography tool, makes measurements, and repeats the process at another user selected position. A measurement made in the ROI in the imaging plane may then be displayed as a value associated with the ROI and be reported in the unit of Young's modulus, for example on a display of the ultrasound elastography system. For example, by this, a liver stiffness value associated with the ROI may be reported in the unit of Young's modulus. By moving the ROI, a user may inspect a liver in a non-invasive manner.

Document US 2011/0066030 A1 shows an example for an ultrasound imaging system providing dynamic control of a shear wave front used to image viscoelasticity in a biological tissue. The system receives an indication of a region of interest and selects a shear wave front shape. The system also selects, based on the selected shear wave front shape, focus locations for a plurality of push pulses and a sequence for moving a shear wave source among the focus locations. The system transmits a series of push pulses according to the selected sequence, and determines a speed of the shear wave front as it passes through the region of interest. Changes in the speed of the shear wave front are related to changes in stiffness within the tissue.

Improper positioning of the region of interest could, however, lead to sub-optimal elastography measurements, in particular for liver fibrosis staging. There are several criteria that go into making the elastography measurement an optimal measurement. For the application of liver fibrosis staging, for example, recommended scan protocols by manufactures usually suggest placing the ROI in a region without and away from artifacts. Elastography measurement results can suffer from the poor placement of the ROI for two reasons. First, shear waves reflected by artifact wall in the lateral direction may contaminate stiffness reconstruction if filtering on reflection is not efficient. Second, the ROI may be placed right behind or in front of an artifact in the depth direction. Strong specular reflection caused by the artifact wall will reduce push pulse energy leading to a lower shear wave signal-to-noise-ratio and unstable stiffness reconstruction.

There is a need to further improve such elastography system.

SUMMARY OF THE INVENTION

It is an object of the present invention to provide an improved ultrasound elastography system and method. It is a further object of the present invention to provide a computer program for implementing such method.

In a first aspect of the present invention an ultrasound elastography system for providing an elastography measurement result of an anatomical site is presented that comprises an ultrasound image acquisition probe configured to provide for ultrasound imaging and shear wave elastography, an ultrasound signal and image processing assembly configured to control the ultrasound image acquisition probe and to provide an ultrasound image of the anatomical site, a user input device enabling a user to define a region of interest within the ultrasound image in which region of interest an elastography measurement is to be conducted, and wherein the ultrasound signal and image processing assembly is further configured to visualize a suitability for shear wave elastography of the region of interest to the user within the ultrasound image and/or to recommend an elastography acquisition plane for conducting shear wave elastography to the user.

In a second aspect of the present invention, an ultrasound elastography method for inspecting an anatomical site with an ultrasound elastography system is presented, the method comprising the steps of acquiring a reference image of the anatomical site, determining at least one recommendation feature representative of a suitability for shear wave elastography of a region of interest in the reference image, and conducting at least one visualizing a suitability for shear wave elastography of a region of interest to a user within an ultrasound image acquired with the ultrasound elastography system, and recommending an elastography acquisition plane for conducting shear wave elastography to the user.

In a third aspect of the present invention a, preferably non-transitory, computer program comprising program code means for causing a computer to carry out the steps of the method according to the second aspect or one of its refinements when said computer program is carried out on a computer.

The basic idea of the invention is to provide a clinical support system that distinguishes the optimal (go) and sub-optimal (no-go) regions in the B-mode image for elastography measurements. The clinical support system may therefore provide superposition of vessel structures and go/no-go regions onto the live B-mode images for real time guidance and/or automatic nearest optimal plane recommendation elastography measurement, in particular in elastography shear wave measurement. In addition, there may be provided a user interface to toggle this feature on/off.

In particular, the anatomical site to be examined is a liver. Hence, for example, liver fibrosis staging may be conducted by use of the ultrasound elastography system.

As further outlined in the following, two approaches to decide upon go/no go regions are suggested, namely the local approach and global approach. In the local approach, once shear wave elastography is activated, automatic image segmentation and vessel delineation will be performed in real-time on the underlying live B-mode image without any prior data or images. If a user sees a ROI box located in a go-zone, he can further press the measurement button to receive a stiffness value. Therefore, the suitability expresses whether a good quality shear wave measurement result can be expected in a that ROI.

A more robust approach to detect recommendation features in an anatomical site, for example the liver, would explore full 3D anatomy. Hence, a second approach is called global approach, in which optimal placement of the ROI box relies on anatomical information achieved prior to the shear wave elastography scan. Such information may be formed by the global hepatic vessel tree structures and/or other anatomical features in the anatomical structure, for example in the 3D liver volume. This approach may require a sensor be placed on the transducer for real-time monitoring of its positions and orientation using electromagnetic or optical tracking systems.

Preferred embodiments of the invention are defined in the dependent claims. It shall be understood that the claimed method has similar and/or identical preferred embodiments as the claimed device and as defined in the dependent claims.

According to a refinement of the system, the ultrasound signal and image processing assembly is further configured to superimpose at least one recommendation feature determined in a reference image onto the ultrasound image and/or to recommend the elastography acquisition plane to the user based on at least one recommendation feature determined in the reference image. Hence, the ultrasound signal and image processing assembly is configured to visualize the suitability for shear wave elastography by superimposing at least one recommendation feature onto the ultrasound image. Such a recommendation feature may be for example a position of a vessel, a homogenous tissue region or a suspicious lesion region in the anatomical structure. Hence, a recommendation feature represents areas of the anatomical site, i.e. go/no-go regions for ultrasound shear wave elastography. The suitability expresses whether a good quality shear wave measurement result can be expected in a certain ROI. Hence, a "go" region for ultrasound shear wave elastography would be suitable. A "no-go" region would be unsuitable, for example as it is too close to a vessel, lesion, or else. By visualizing these recommendation features in the ultrasound image, guidance may be provided to a user. Further, by knowing about the recommendation features, a recommendation for an ultrasound shear wave elastography measurements can be made. By this, the user has a clear guidance concerning go and no-go areas for elastography measurements within the ultrasound image. The recommendation feature may be a region highlighted in the image. Further, a plane for elastography measurement, in particular next to a current position of an ultrasound image acquisition probe, may be presented to a user. Hence, the user may alter a position and/or orientation of the probe to achieve better measurement results.

According to a refinement of the system, the ultrasound signal and image processing assembly is further configured to generate the at least one recommendation feature by segmenting at least one vessel in a reference image. By this, shear waves reflected by vessel wall near the ROI that could contaminate stiffness reconstruction if filtering on reflection is not efficient may be avoided.

According to a refinement of the system, the ultrasound signal and image processing assembly is further configured to generate the at least one recommendation feature by detecting and segmenting a homogenous tissue region in a reference image. This may further contribute to avoid problems with stiffness reconstruction by suggesting regions of homogenous tissue as go-areas.

According to a refinement of the system, the ultrasound signal and image processing assembly is further configured to generate the at least one recommendation feature by detecting a lesion region in a reference image, wherein the lesion region plus a margin region encompassing the lesion region is generated as the recommendation feature. By this, depending on its size relative to the size of the ROI box and its boundary conditions, suspicious lesions such as liver cysts and tumors that are close to the ROI box in the lateral direction may cause some artifacts to shear wave measurement mainly due to shear wave reflection at the boundary. In this case, detection of such lesions can be done in a local approach. Basically the system can define a bigger region centered at the measurement ROI with a pre-determined safety margin. Hence, better measurement results may be achieved.

According to a refinement of the system, the ultrasound image is a two-dimensional B-mode ultrasound image. In particular, it may be a live two-dimensional B-mode ultrasound image. By this, the visualization of the recommendation features may be provided directly in the live acquired ultrasound images. Hence, a user may make use of the recommendations during the usual examination procedure.

According to a refinement of the system, the reference image is a two-dimensional B-mode ultrasound image. By this, no further capabilities of the ultrasound are necessary. A common B-mode ultrasound image may be used, for example, to segment vessels present within the plane of the B-mode image. In particular, the live B-mode ultrasound image may be used. Hence, the reference image may be the ultrasound image, as defined in the previous paragraph.

According to a refinement of the system, the reference image is a three-dimensional image of the anatomical site. By this, it may be possible to better segment complete vessel structures within the anatomical structure to be examined. In particular, this may help to find a plane to recommend to the user for conducting the ultrasound elastography measurement.

According to a refinement of the system, the reference image is a three-dimensional image acquired via a modality different from ultrasound image acquisition, wherein the reference image is stored in a memory unit of the ultrasound signal and image processing assembly. By this, better quality three-dimensional images the anatomical structure may be acquired prior to the ultrasound measurement, for example via computer tomography or magnetic resonance tomography. Better segmentation results may be acquired which— when registered with a live B-mode ultrasound image during examination—may form the basis for recommendation features superimposed on the live B-mode image.

According to a refinement of the system, the ultrasound image acquisition probe and the ultrasound signal and image processing assembly are further configured to enable a user to acquire the three-dimensional ultrasound image of the anatomical site. By this, no further modality such as computer tomography or magnetic resonance tomography is necessary. Three-dimensional ultrasound images may be used to provide the recommendation features for sue during the two-dimensional live B-mode imaging.

According to a refinement of the system, the ultrasound signal and image processing assembly is further configured to register the at least one recommendation feature and the ultrasound image via image processing. By this, it is ensured that the recommendation features suit the live ultrasound images in position and orientation. Pure computation-based registering method may be applied as they are well known in the art.

According to a refinement of the system, the system further comprises a tracking device to track a position and orientation of the ultrasound image acquisition probe and to support registering the at least one recommendation feature to the ultrasound image. In particular, the tracking device may be an electromagnetic tracking device or an optical tracking device. By this, the position and orientation of the image acquisition probe may be tracked. By knowing its position and orientation, it is again possible to register the live ultrasound images and the recommendation features determined by use of three-dimensional images acquired earlier. Further, a current position and orientation of the ultrasound image acquisition probe can be tracked for better guidance of the user towards an optimal elastography acquisition plane to the user.

According to a refinement of the system, the user input device is further configured to enable the user to toggle the visualization of the suitability for shear wave elastography of a region of interest within the ultrasound image and/or the recommendation of an elastography acquisition plane for conducting shear wave elastography to the user on and off. By this, the user may switch on an off the recommendations in the ultrasound image during examination.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
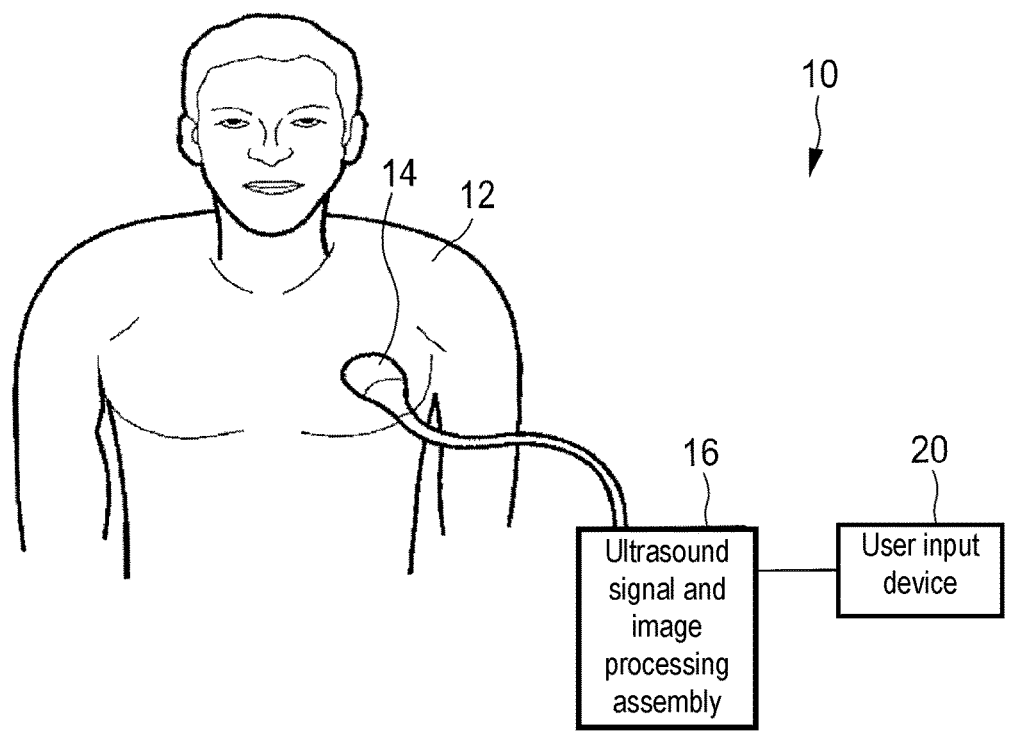
FIG. 1 shows a schematic illustration of embodiment of an ultrasound elastography system.

FIG. 1 shows a schematic illustration of an ultrasound elastography system 10 according to an embodiment. The ultrasound elastography system 10 is applied to inspect a anatomical site of an anatomical site, in particular an anatomical site of a patient 12. The ultrasound elastography system 10 is also for providing an elastography measurement result of the anatomical site. The system comprises an ultrasound image (52) acquisition probe (14) configured to provide for ultrasound imaging and shear wave elastography and an ultrasound signal and image processing assembly configured to control the ultrasound image acquisition probe 14 and to provide an ultrasound image of the anatomical site. Further, the system 10 comprises a user input device 20, for example for enabling a user to define a region of interest within the ultrasound image in which region of interest an elastography measurement is to be conducted. Furthermore, the ultrasound signal and image processing assembly 16 is configured to visualize a suitability for shear wave elastography of the region of interest to the user within the ultrasound image 52 and/or to recommend an elastography acquisition plane for conducting shear wave elastography to the user.

Figure 2:
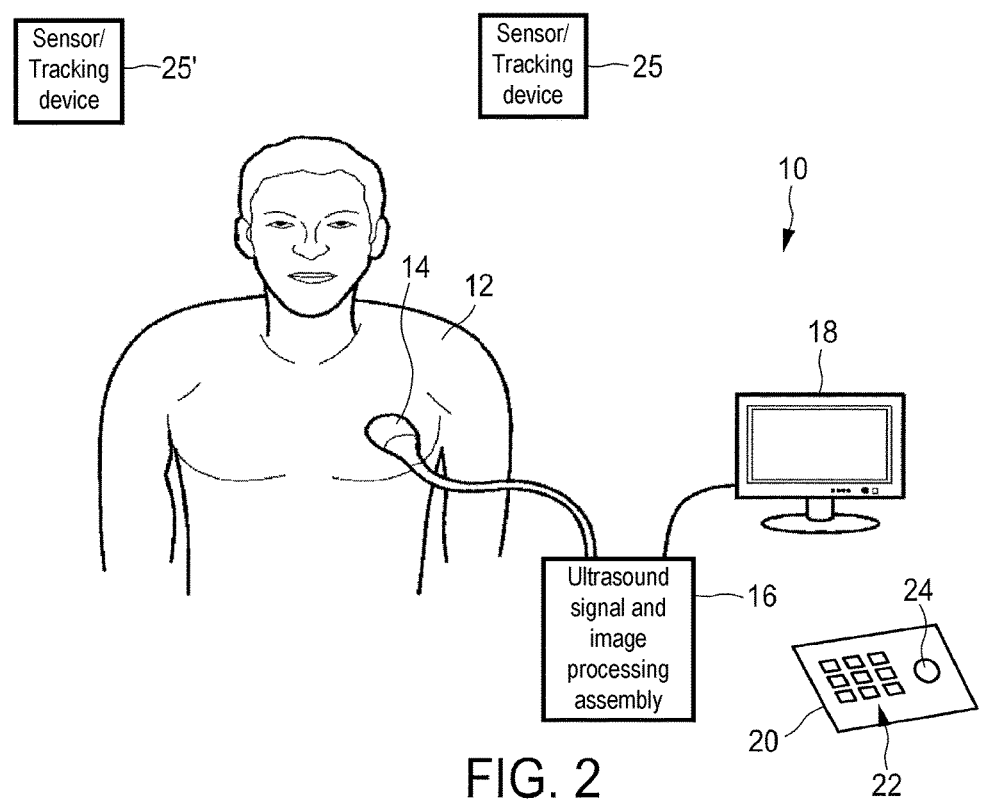
FIG. 2 shows a schematic illustration of a further embodiment of an ultrasound elastography system.

FIG. 2 shows a schematic illustration of an ultrasound elastography system 10 according to a further embodiment, in particular a medical ultrasound three-dimensional imaging system. The ultrasound elastography system 10 is applied to inspect a anatomical site of an anatomical site, in particular an anatomical site of a patient 12. The ultrasound elastography system 10 comprises an ultrasound image acquisition probe 14 having at least one transducer array having a multitude of transducer elements for transmitting and/or receiving ultrasound waves. In one example, the transducer elements each can transmit ultrasound waves in form of at least one transmit impulse of a specific pulse duration, in particular a plurality of subsequent transmit pulses. The transducer elements can for example be arranged in a one-dimensional row, for example for providing a two-dimensional image that can be moved or swiveled around an axis mechanically. Further, the transducer elements may be arranged in a two-dimensional array, in particular for providing a multi-planar or three-dimensional image.

In general, the multitude of two-dimensional images, each along a specific acoustic line or scanning line, in particular scanning receive line, may be obtained in three different ways. First, the user might achieve the multitude of images via manual scanning. In this case, the ultrasound image acquisition probe may comprise position-sensing devices that can keep track of a location and orientation of the scan lines or scan planes. However, this is currently not contemplated. Second, the transducer may be automatically mechanically scanned within the ultrasound image acquisition probe. This may be the case if a one dimensional transducer array is used. Third, and preferably, a phased two-dimensional array of transducers is located within the ultrasound image acquisition probe and the ultrasound beams are electronically scanned. The ultrasound image acquisition probe may be hand-held by the user of the system, for example medical staff or a doctor. The ultrasound image acquisition probe 14 is applied to the body of the patient 12 so that an image of an anatomical site 32 in the patient 12 is provided.

Further, the ultrasound elastography system 10 has an ultrasound signal and image processing assembly 16 that controls the provision of an ultrasound image via the ultrasound elastography system 10. The ultrasound signal and image processing assembly 16 controls not only the acquisition of data via the transducer array of the ultrasound image acquisition probe 14 but also signal and image processing that form the ultrasound images out of the echoes of the ultrasound beams received by the transducer array of the ultrasound image acquisition probe 14.

The ultrasound elastography system 10 further comprises a display 18 for displaying the three-dimensional images to the user. Further, an input device 20 is provided that may comprise keys or a keyboard 22 and further input devices, for example a track ball 24. The input device 20 might be connected to the display 18 or directly to the ultrasound signal and image processing assembly 16.

Further, the ultrasound elastography system 10 comprises a tracking device, for example an electromagnetic tracking device. Parts of the tracking device are situated within the probe 14 or may be associated with the probe via a clip. Further parts 25, 25', for example sensors like magnetoresistive sensors or optical sensors, may be placed in the circumference of the ultrasound elastography system. Preferably, the spatial coordinates of the further parts 25, 25' are known.

Figure 3:
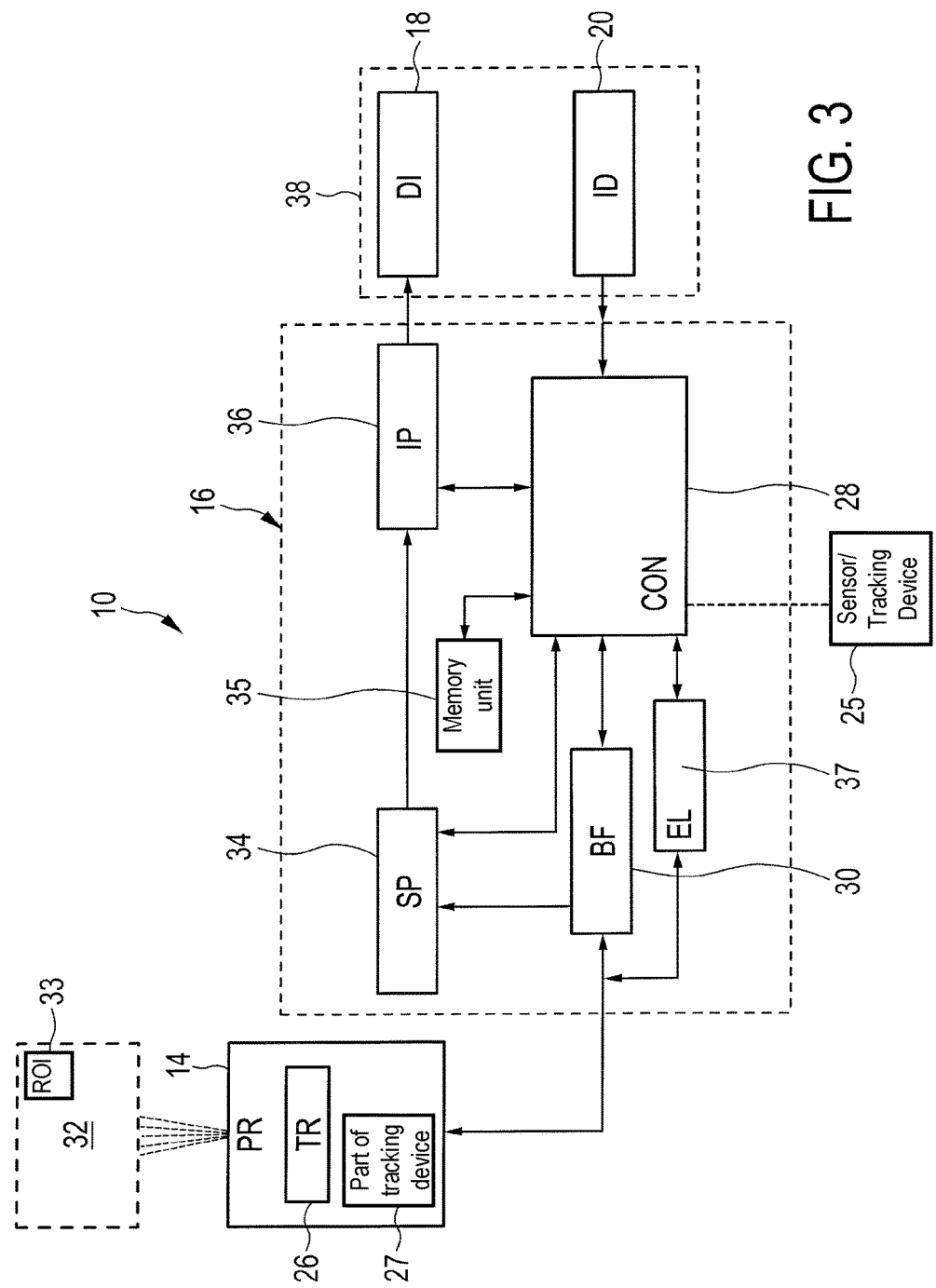
FIG. 3 shows a block diagram illustrating the different components of an exemplary ultrasound elastography system.

FIG. 3 shows a schematic block diagram of the ultrasound elastography system 10. As already laid out above, the ultrasound elastography system 10 comprises an ultrasound image acquisition probe (PR) 14, the ultrasound signal and image processing assembly (CU) 16, the display (DI) 18 and the input device (ID) 20. As further laid out above, the probe (PR) 14 comprises a transducer array 26, for example a phased two-dimensional transducer array or automatically scanned one-dimensional transducer array. Further, the probe may comprise a part 27 of the tracking device, for example a coil that generates an electromagnetic field that is sensed via the sensors 25, 25'. In general, the ultrasound signal and image processing assembly (CU) 16 may comprise a central processing unit that may include analog and/or digital electronic circuits, a processor, microprocessor or the like to coordinate the whole image acquisition and provision. Further, the ultrasound signal and image processing assembly 16 comprises a herein called central processing unit 28. However, it has to be understood that the central processing unit 28 does not need to be a separate entity or unit within the ultrasound elastography system 10. A memory unit is indicated by reference numeral 35. It can be a part of the ultrasound signal and image processing assembly 16 and generally be hardware or software implemented. The current distinction is made for illustrative purposes only. The central processing unit (CON) 28 as part of the ultrasound signal and image processing assembly 16 may control a beam former and, by this, what images of the anatomical site 32 are taken and how these images are taken. The beam former (BF) 30 generates the voltages that drives the transducer array (TR) 26, determines parts repetition frequencies, it may scan, focus and apodize the transmitted beam and the reception or receive beam(s) and may further amplify filter and digitize the echo voltage stream returned by the transducer array 26. Further, the central processing unit 28 of the ultrasound signal and image processing assembly 16 may determine general scanning strategies. Such general strategies may include a desired anatomical site acquisition rate, lateral extent of the anatomical site, an elevation extent of the anatomical site, maximum and minimum line densities, scanning line times and the line density as already explained above. The beam former 30 further receives the ultrasound signals from the transducer array 26 and forwards them as image signals.

A shear wave elastography subsystem is designated with reference numeral 37. The shear wave subsystem 37 allows the ultrasound imaging system 10 to operate in a shear wave mode. In certain embodiments, the shear wave subsystem 37 determines the focus locations and sequence for moving a shear wave source among the focus locations. In addition, or in other embodiments, the shear wave subsystem 37 performs the other functions described herein with respect to dynamically controlling the shear wave front. An artisan will recognize from the disclosure herein that the shear wave subsystem 37 may be combined with other components of the system 10. For example, at least some of the functions described for the shear wave subsystem 37 may be performed by the CON 28. For tissue quantification according to one embodiment, the shear wave subsystem 37 may allow the user of the ultrasound imaging system 10 to identify an anatomic location for measurement using a region of interest marker placed on an ultrasound image. An acoustic push pulse is applied just lateral to this location, inducing a shear wave that travels through the region of interest. Tracking beams, sensitive to greater than $\frac{1}{100}$ the wavelength of sound, are applied to the pulse path. The tracking beams are continuously transmitted until the passing shear wave front is detected. The time between generation of the shear wave and detection of the peak is utilized to compute the shear wave velocity. Multiple measurements are made for a given spatial location before a value is reported in order to ensure measurement quality.

Further, the ultrasound elastography system 10 comprises a signal processor (SP) 34 that receives the image signals. The signal processor 34 is generally provided for analogue-to-digital-converting, digital filtering, for example, band pass filtering, as well as the detection and compression, for example a dynamic range reduction, of the received ultrasound echoes or image signals. The signal processor forwards image data.

Further, the ultrasound elastography system 10 comprises an image processor (IP) 36 that converts image data received from the signal processor 34 into display data finally shown on the display 18. In particular, the image processor 36 receives the image data, preprocesses the image data and may store it in an image memory. These image data is then further post-processed to provide images most convenient to the user via the display 18. In the current case, in particular, the image processor 36 may form the three-dimensional images out of a multitude of two-dimensional images in each slice.

A user interface is generally depicted with reference numeral 38 and comprises the display 18 and the input device 20. It may also comprise further input devices, for example, a mouse or further buttons which may even be provided on the ultrasound image acquisition probe 14 itself.

A particular example for an ultrasound elastography system which may apply the current invention is a system applying the Philips ultrasound new release shear wave Elastography Point Quantification (ElastPQ).

Hence, there may be provided an ultrasound elastography system 10 that distinguishes the optimal (go) and suboptimal (no-go) regions in an B-mode ultrasound image for elastography measurements. The system 10 may, in particular, comprise the features of super position of vessel structures and go/no-go regions onto the live B-mode images for real time guidance and automatic nearest optimal plane recommendation for elastography measurement. In addition, the invention also includes a user interface 38 to toggle this feature on/off.

To main approaches to provide this may be implemented, in particular to decide go/no go regions, namely the local and global approach. In the local approach, once the shear wave elastography feature is activated, automatic image segmentation and vessel delineation will be performed in real-time on the underlying live B-mode image without any prior data or images. If the user sees the measurement box located in the go-zone, he can further press the measurement button to get the stiffness value. The system 10 using this local approach may comprise the main elements of an ultrasound system, a 1-D or 2-D transducer that is capable of conventional B-mode imaging and shear wave elastography and a support application run on the ultrasound signal and processing assembly that comprises the components to assist the user with go/no-go regions for elastography measurement. These may include at least one of a group consisting of segmentation of vessels in the live 2D B-mode images that are used for elastography, detection and segmentation of homogenous regions that are used for elastography, and superposition of vessel structures and "suspicious" lesion region with a small surrounding margin, for example in the order of 1 cm, onto the live B-mode images as no/go region for real time guidance.

The system 10 using the global approach may comprise the main elements of an ultrasound system, a 1-D or 2-D transducer that is capable of conventional B-mode imaging and shear wave elastography, a 3D image of the anatomical structure to be examined, for example a liver, acquired by sweeping 1D ultrasound transducer, or 2D ultrasound transducer, or previously acquired 3D images by other modalities such as computer tomography or magnetic resonance tomography. Further, a tracking system, for example an electromagnetical or optical tracking system should be present. Further, a support application may be run on the ultrasound signal and processing assembly that comprises the components to assist the user with go/no-go regions for elastography measurement. These may include at least one of a group consisting segmentation of vessels in the pre-procedural images (3D Ultrasound and/or prior CT), registration, motion compensation, and super position of these 3D vessel structures on the live 2D B-mode images that are used for elastography; detection and segmentation of homogenous regions within the liver in the 3D ultrasound, and its registration, and motion compensation with the live B-mode images; and superposition of vessel structures and "suspicious" lesion region with a small surrounding margin (in the order of 1 cm) onto the live B-mode images for real time guidance.

Figure 4:
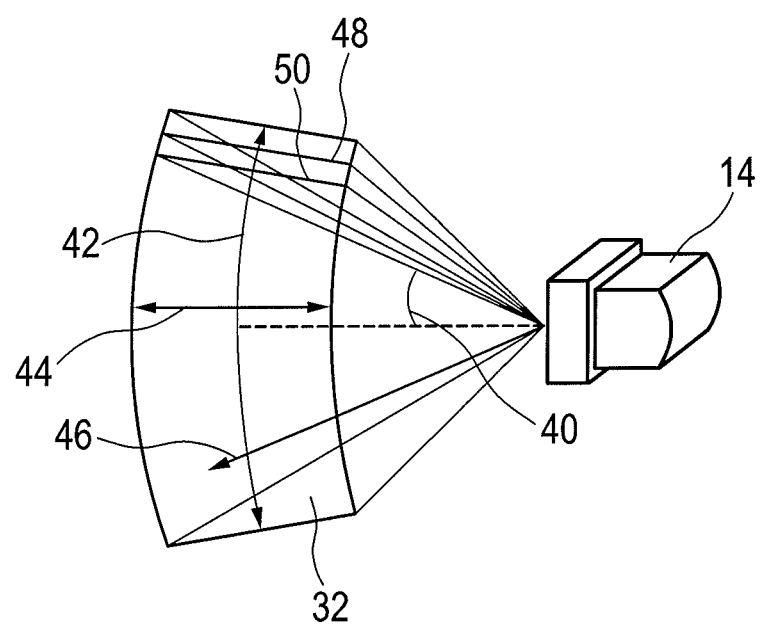
FIG. 4 shows a schematic illustration showing planes and angles in ultrasound volume scanning.

FIG. 4 shows an example of an anatomical site 32 relative to the ultrasound image acquisition probe 14. The exemplary anatomical site 32 depicted in this example is of a sector type, due to the transducer array of the ultrasound image acquisition probe 14 being arranged as a phased two-dimensional electronically scanned array. Hence, the size of the anatomical site 32 may be expressed by an elevation angle 42 and a lateral angle 44. A depth 46 of the anatomical site 32 may be expressed by a so-called line time in seconds per line. That is the scanning time spent to scan a specific scanning line.

The anatomical site 32 may be divided into a multitude of slices 48, 50 or two-dimensional images. Only two slice 48, 50 are depicted for illustrative purposes. Actually, a multitude of planes or slices 48, 50 having different elevational angles 40 are spread over the volume of the anatomical site 32. Of course, the slices 48, 50 may also be oriented in the elevational direction and spread across the anatomical site 32 in the lateral direction. During image acquisition, the two-dimensional transducer array of the ultrasound image acquisition probe 14 is operated by a beam former in a way that the anatomical site 32 is scanned along a multitude of these scan lines within each of the slices 48, 50 sequentially. In multi-line receive processing, a single transmit beam might illuminate a multitude, for example four, receive scanning lines along which signals are acquired in parallel. If so, such sets of receive lines are then electronically scanned across the anatomical site 32 sequentially.

Figure 5:
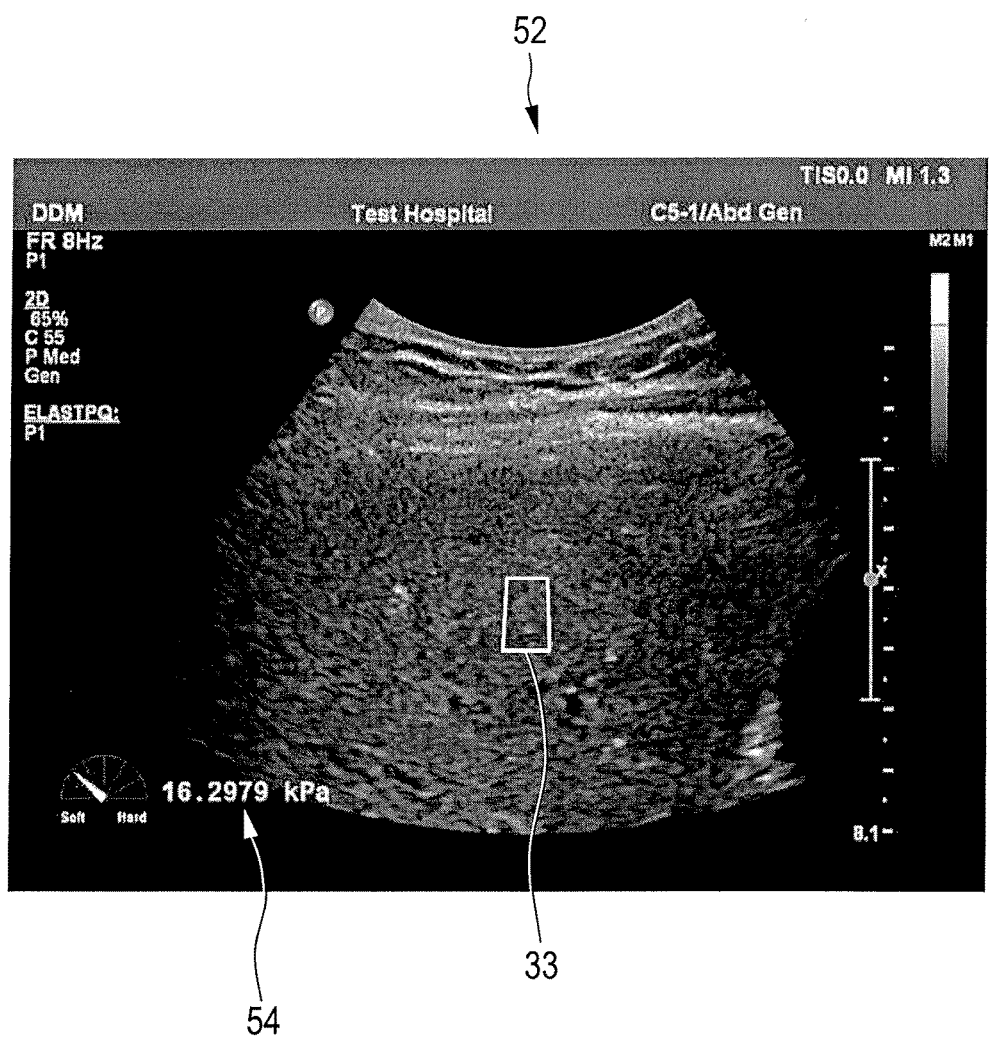
FIG. 5 shows an example of a B-mode image with an ROI for an elastography measurement.

FIG. 5 shows an ultrasound image 52 that is a conventional B-mode ultrasound image. The ultrasound image is two-dimensional and could, for example, be acquired with the system 10 as explained above. Further, it is shown a region of interest 33 which a user may use to select a certain point within the B-mode image 52 for elastography measurement. After a user selects a certain region of interest 33 within the image 52, an elastography measurement is conducted and a result is displayed as value in the image 52 which value is generally designated by reference numeral 54. By this, the user may evaluate different portions of the B-mode image 52 to map the tissue elasticity over the B-mode image. While in FIG. 5 a proper placement of a region of interest 33 is shown, this may not always be the case.

Figure 6:
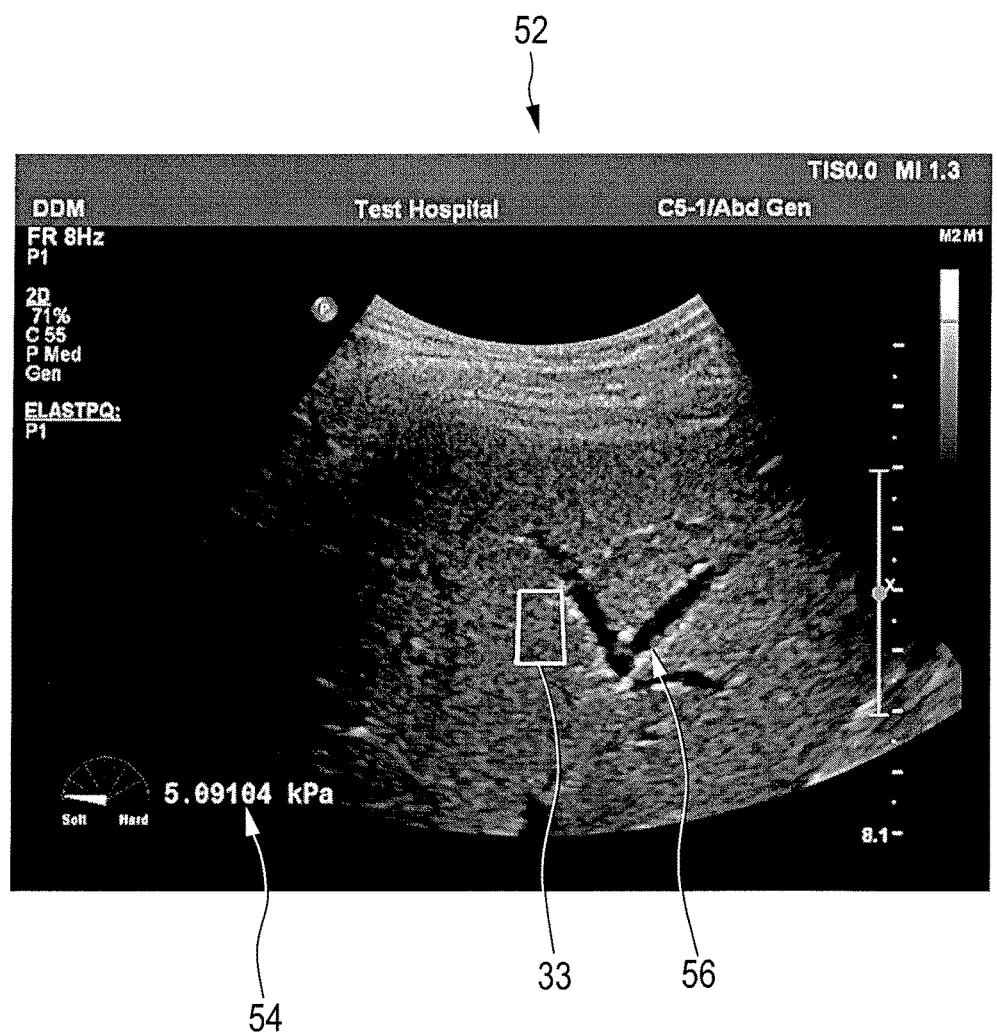
FIG. 6 shows an example of a B-mode image with an ROI for an elastography measurement and adjacent vessel structure.

In FIG. 6 there is shown a comparable B-mode image 52 in which an elasticity value 54 is shown. Further, again, a region of interest 33 is shown. However, in this case, the region of interest 33 is placed closely to a vessel 56. However, by reflections from the vessel 56, proper elasticity measurement may be not possible. Further, besides vessels 56 viewable within the image 52, it may also be the case that a vessel is placed closely to the region of interest 33 in the depth region of the image 52 so that the adjacent vessel 56 may not be clearly viewable in the image 52.

Figure 7:
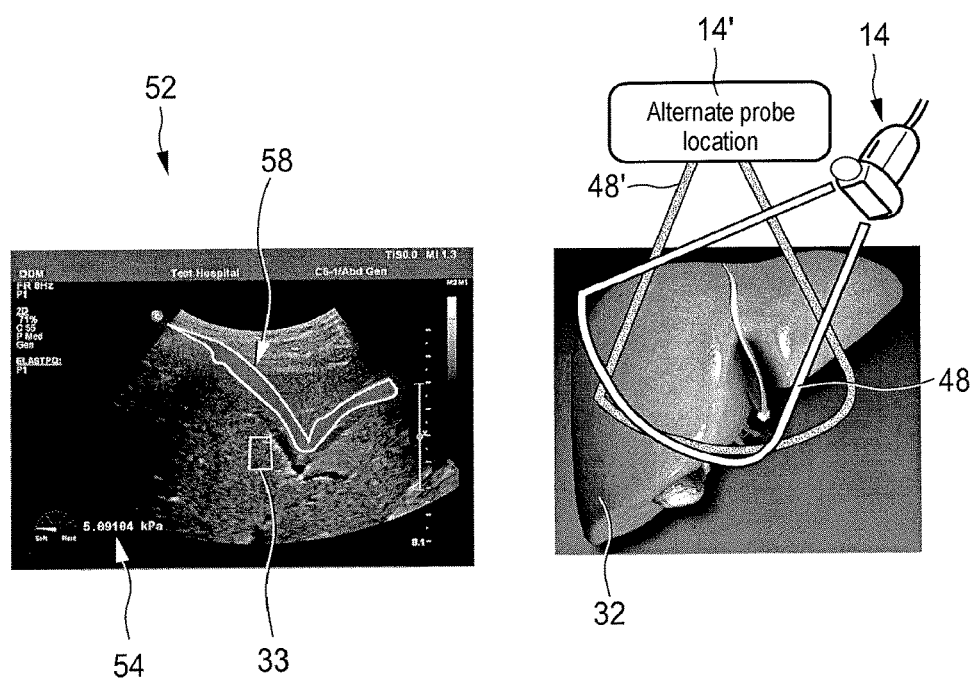
FIG. 7 shows an example of a B-mode ultrasound image with superimposed recommendation features, and an illustration of a plane recommendation for an improved elastography measurement.

FIG. 7 shows the two embodiments of a final presentation to the user according to embodiments. In one embodiment, the vessel structure along with the go/no-go regions or recommendation features 58 can be superimposed on the live B-mode image 52, in particular using tracking based or image based registration techniques. The superimposed image 52 can also be compensated for respiratory motion using motion compensation techniques. Further, in case it is detected that a plane 48 is improper for elastography scanning, the closest optimal plane 48' may be suggested to a user so that the image acquisition probe may be properly positioned at 14'.

Figure 8:
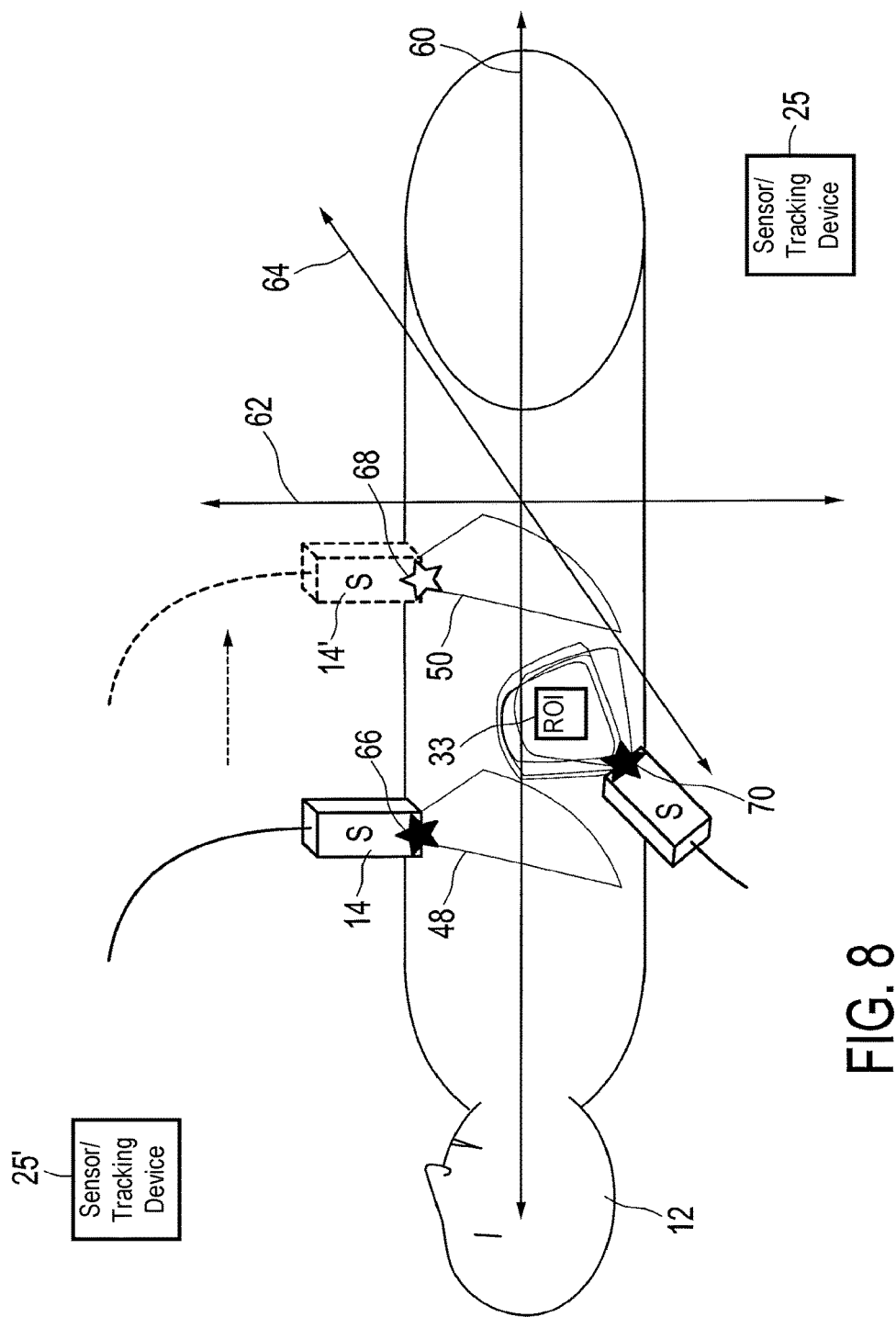
FIG. 8 shows a further illustration of a plane recommendation for an improved elastography measurement.

FIG. 8 shows a schematic illustration of the body of a patient 12. The cranio-caudal axis is designated with reference numeral 60. The anterior-posterior axis is designated with reference numeral 62. The left-right axis is designated with reference numeral 64. The user moves the probe to a first position 66 which is tracked by the tracking device 25, 25'. This may be conducted, for example, by an electromagnetic tracking device or an optical tracking device. Instead of moving the image acquisition probe 14 to a second position 68 on the patient, the system 10 may recommend to the user moving the image acquisition probe 14 to a third position 70 having a different orientation to provide a better view on the liver and better elastography results. Tracking the movement to the third position 70, an elastography measurement could then be initiated when the third position 70 is reached properly. After this, the elastography measurement of the ROI in the anatomical structure 32 can take place as usual.

Figure 9:
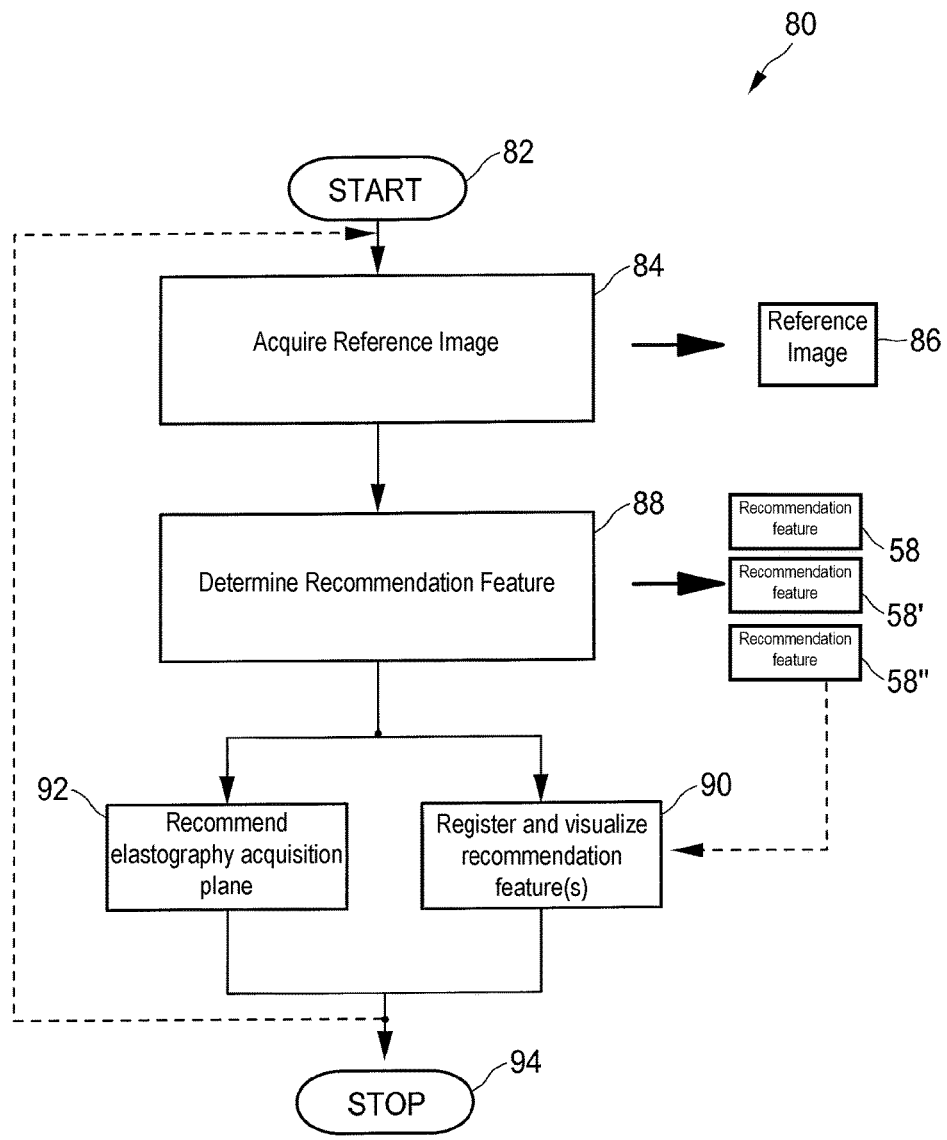
FIG. 9 shows an embodiment of an ultrasound elastography method.

FIG. 9 shows an embodiment 80 of a method for inspecting an anatomical site 32 with an ultrasound elastography system 10. The method starts at step 82. In step 84, a reference image 86 of the anatomical site 32 is acquired. This may be conducted using a further modality like computer tomography or magnetic resonance tomography. However, it may also be the case that the reference image 86 is acquired via the ultrasound system 10. Further, a reference image 86 acquired via ultrasound may two-dimensional or three-dimensional. Then, in a step 88, at least one recommendation feature 58 representative of a suitability for a shear wave elastography of a region of interest 33 in the reference image 86 is determined. Such a recommendation feature 58 may be for example a position of vessels, homogenous tissue regions or suspicious lesion regions in the anatomical structure.

Then, at least one of the following two steps is conducted. The recommendation features 58 may either be used to recommend an elastography acquisition plane for conducting shear wave elastography to the user, this may be conducted in step 92. Alternatively or additionally, the recommendation features 58 may be registered and visualized in step 90 within an ultrasound image 52 acquired with the ultrasound elastography system 10 to provide an information on a suitability for shear wave elastography in a region of interest 33 within the ultrasound image 52 to the user.

The method may then be repeated as long as ultrasound examination is conducted or may end in step 94.

Figure 10:
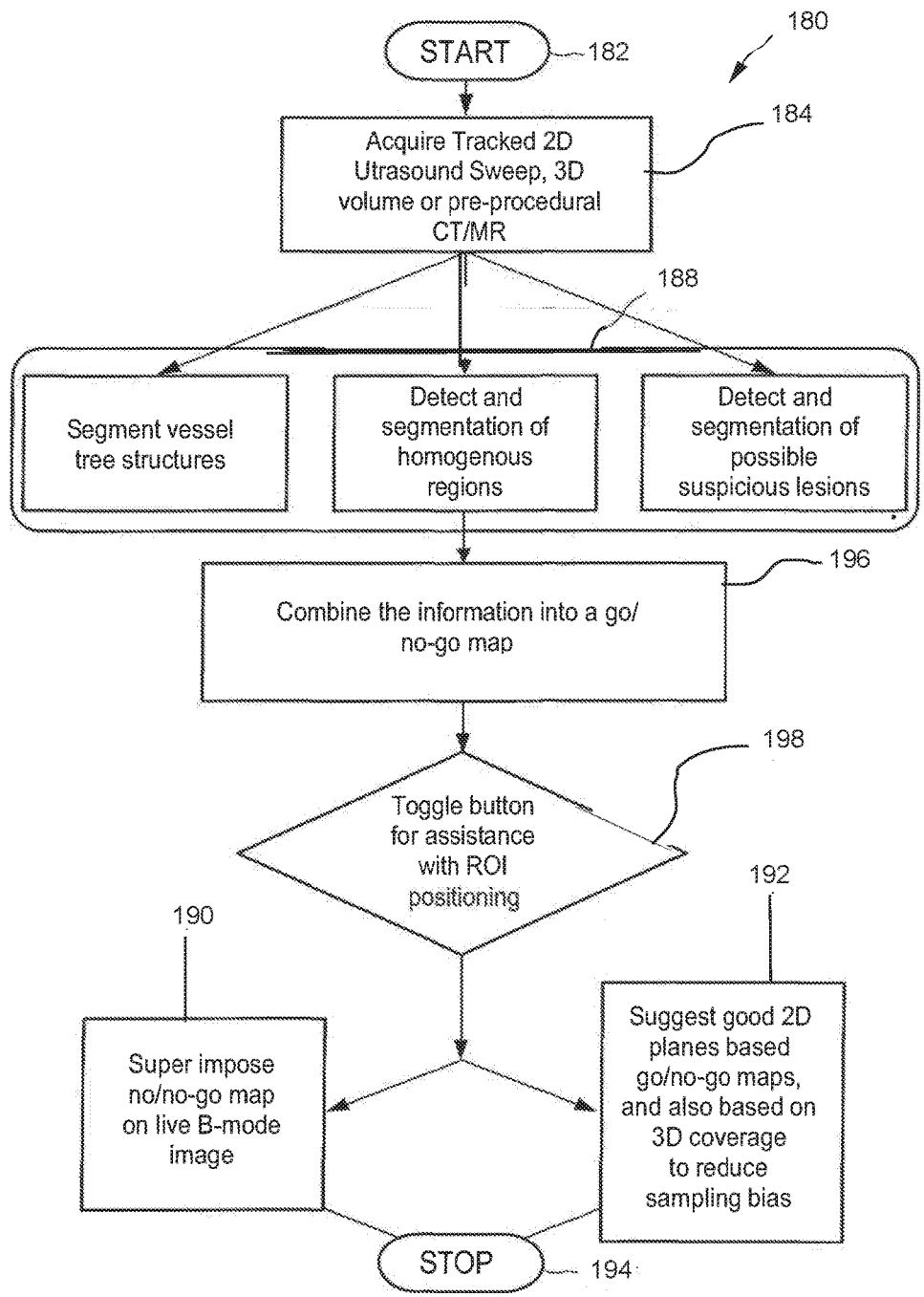
FIG. 10 shows a further embodiment of an ultrasound elastography method.

In FIG. 10, a further embodiment 180 of a method is shown.

In this embodiment, the local and global approaches take the steps 190 to 194 similarly toward vessel delineation, homogeneous area detection, visualizing go/no-go zone on B-mode ultrasound image 52, and toggling the proposed feature on and off. In step 184, the acquisition and integration of a live 2D/3D ultrasound image to pre-procedure images is conducted. This can be achieved using a variety of different tracking techniques. In one embodiment, the tracking could be electromagnetic tracking wherein the probe and patient are tracked live in an electromagnetic field. The pre-procedures images could be either tracked three-dimensionally to reconstruct three-dimensional ultrasound images/volumes. Alternatively, earlier acquired MR/CT images could be used. These pre-procedure images can be registered to the electromagnetic tracking system using fiducials, for example. Using this integration, a variety of different visualization techniques can be enabled.

Then, steps 188 and 196 combined may form the core of the determination and visualization of an optimal ROI based on go/no-go regions. This comprises four components— three of them, depicted in step 188, are detection and segmentation of recommendation features 58 that decide the optimal regions, and fourth, step 196, is the integration of these recommendation features 58 extracted from the three detection modules.

In vessel structure delineation, there are identified three embodiments of vessel structure delineation, which can be used either independently or together to form an estimate of topography of the vessel structures. Major blood vessels in an example of a liver include hepatic artery, hepatic vein and portal vein. In ultrasound B-mode imaging, vessels are visible as relatively hypoechoic structures. There are also a couple of vessel look like structures namely common bile duct and gallbladder on the B-mode. These are all classified as no-go zone for shear wave measurement, in particular for the application of liver fibrosis assessment. Several specific methods have been proposed to do liver vessel structure segmentation in 3D CT, MR and Ultrasound images. These methods apply one or combine a multitude of the following segmentation techniques: intensity thresholding, region growing, level-set, deformable model fitting, and geometrical moments. They can either be completely automatic methods or manually supported delineation methods.

In addition to vessels, inhomogeneous regions near by the ROI location should also be identified. Depending on its size relative to the size of the ROI box and its boundary conditions, suspicious lesions such as liver cysts and tumors that are close to the RIO in the lateral direction may cause some artifacts to shear wave measurement mainly due to shear wave reflection at the boundary. In this case, detection of such lesions can be done in a focal approach. Basically the system can define a bigger region centered at the measurement ROI with a pre-determined safety margin. Using texture analysis methods, for example first order statistics, gray-level co-occurrence matrix (GLCM), gray-level run-length matrix (GLRLM) and gray level difference matrix (GLDM), the ultrasound system 10 can determine if there is a significant discontinuity existing in the surrounding area of the shear wave measurement ROI, and further guide the user whether that is go or no-go region.

Furthermore, the vessels can be identified by using the color flow mode. A mixture of recommendation features visualized in B-mode images and color flow pulses can be used to in conjunction to identify the locations of the major vessels.

In step 196, the information from step 188 can be combined to make a combined map of optimal and sub-optimal regions for elastography measures.

Steps 190 and 192 show the output of the system 10 to the user. Before, assistance in ROI positioning may be toggled on or off in a step 198. Besides the visualization of the recommendation features 58 in step 190, additionally or alternatively, the next closest optimal plane can be computed by combining a combined optimal map of step 96 with the actual tracking information of the image acquisition probe 14, and displayed to the user. Since the probe is tracked, the position of the 2D image plane in the 3D context is already known. Three inputs go into the automatic suggestion of closest possible acquisition plane. These are the current tracked position the image acquisition probe 14, regions in 3D where the elastography measurements have already been made and go/no-go regions as recommendation features 58 computed in the previous steps 188 and 196. Given these three inputs, optimal plane closest to current position of the probe 14 can be determined and displayed to the user.

Figure 11:
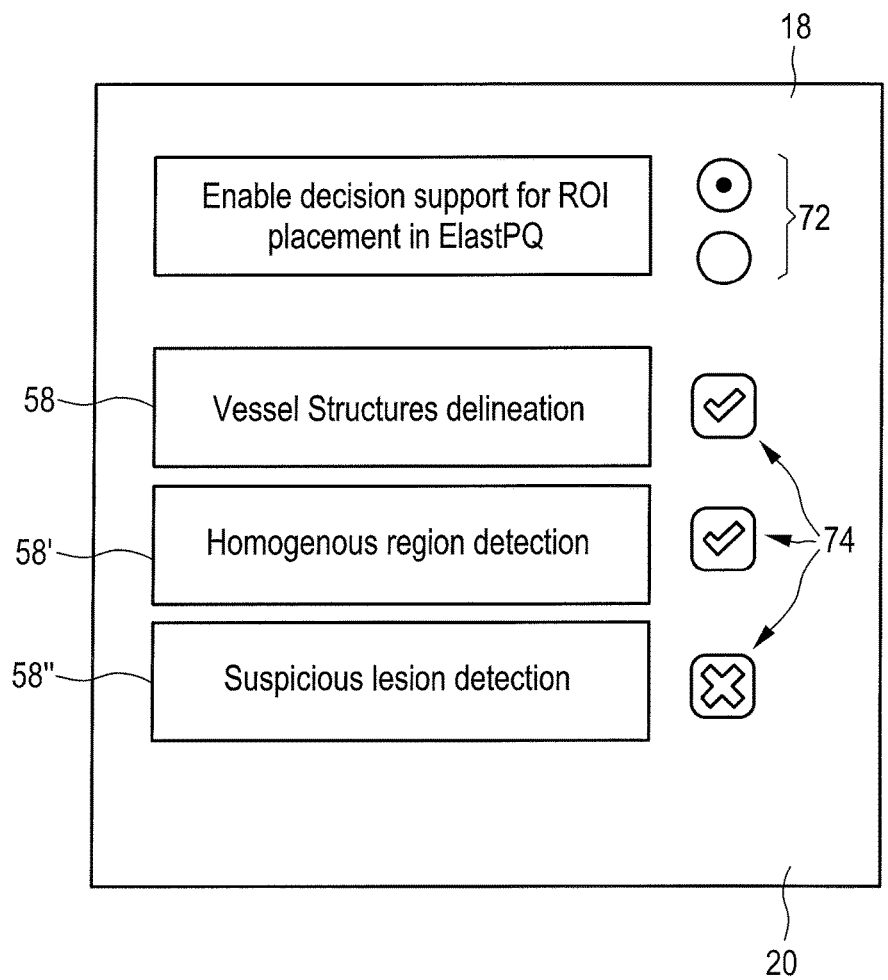
FIG. 11 shows a possible input device display for toggling the visualization of the recommendation features.

In FIG. 11, when the overall decision support is activated, the user can pick and choose what kind of decision support is needed. In the above example, the user has selected to choose vessel structure delineation and homogenous regions detection, but not suspicious lesion detection. The three modules can operate independently depending on the use selection. Each of these features can be switched on/off using such a user interface as shown below in FIG. 11 (step 198 in the flowchart of FIG. 10).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound elastography system for ultrasonically inspecting an anatomical site, the system comprising:
    an ultrasound image acquisition probe configured to transmit ultrasound toward the anatomical site; and
    a processing circuit configured to generate an ultrasound image of the anatomical site responsive to signals received from the ultrasound image acquisition probe, wherein the processing circuit is further configured to:
    control the ultrasound image acquisition probe to transmit a push pulse for generating a shear wave within the anatomical site;
    identify, from a B-mode reference image, first and second non-overlapping regions of the anatomical site, wherein the first non-overlapping region is determined to correspond to a region without artifacts for shear wave elastography and the second non-overlapping region is determined to correspond to a region including an artifact that interferes with shear wave elastography, wherein the first and second non-overlapping regions are identified, at least in part, by segmenting the B-mode reference image to identify one or more boundaries between anatomical structures within the anatomical site such that the second region is defined at least in part by the one or more boundaries;
    cause the ultrasound image to be displayed;
    provide at least one recommendation feature with the ultrasound image, wherein the at least one recommendation feature comprises a graphic superimposed on the ultrasound image and delineating the second non-overlapping region, and
    provide an instruction for selecting an elastography acquisition plane different from an image plane of the ultrasound image, or a combination thereof.

2. The system according to claim 1, wherein the processing circuit is further configured to generate the at least one recommendation feature by segmenting the reference image to identify at least one vessel in the reference image.

3. The system according to claim 1, wherein the processing circuit is further configured to generate the at least one recommendation feature by detecting and segmenting a homogenous tissue region in a reference image.

4. The system according to claim 1, wherein the processing circuit is further configured to generate the at least one recommendation feature by segmenting the reference image to identify a lesion region in the reference image, wherein the lesion region plus a margin region encompassing the lesion region is generated as the at least one recommendation feature.

5. The system according to claim 1, wherein the ultrasound image is a two-dimensional B-mode ultrasound image.

6. The system according to claim 1, wherein the reference image is a two-dimensional B-mode ultrasound image.

7. The system according to claim 1, wherein the reference image is a three-dimensional image of the anatomical site.

8. The system according to claim 1, wherein the reference image is a three-dimensional image acquired via a modality different from ultrasound image acquisition, wherein the reference image is stored in a memory circuit of the ultrasound signal and image processing assembly.

9. The system according to claim 1, wherein the processing circuit is further configured to register the at least one recommendation feature and the ultrasound image via image processing.

10. The system according to claim 9, wherein the processing circuit is further configured to track a position and orientation of the ultrasound image acquisition probe for registering the at least one recommendation feature to the ultrasound image.

11. The system according to claim 1, wherein the ultrasound elastography system is further configured to provide a user interface to enable a user to activate functions of the processing circuit associated with the generating of the at least one recommendation feature.

12. The system according to claim 1, wherein the artifact is a blood vessel.

13. The system according to claim 1, wherein the artifact is a lesion.

14. An ultrasound elastography method comprising:
    generating, responsive to ultrasound transmitted by a probe of an ultrasound elastography system, an ultrasound image of an anatomical site;
    identifying, by a processing circuit of the ultrasound elastography system, first and second non-overlapping regions in a B-mode reference image of the anatomical site, wherein the first non-overlapping region is determined by the processing circuit to be free of artifacts for shear wave elastography and wherein the second non-overlapping region is determined by the processing unit to include an artifact that interferes with shear wave elastography, and wherein the first and second non-overlapping regions are identified by the processing unit, at least in part by, by segmenting the B-mode reference image to identify one or more boundaries between anatomical structures within the anatomical site such that the second non-overlapping region is defined at least in part by the one or more boundaries; and
    providing a recommendation feature with the ultrasound image, wherein the recommendation feature comprises a graphic delineating the second non-overlapping region on the ultrasound image, an instruction for selecting an elastography acquisition plane different from a current image plane of the ultrasound image, or a combination thereof.

15. A computer readable medium comprising executable instructions for causing an elastography system to carry out the method as recited in claim 14 when said executable instructions are carried out by a processor circuit of the elastography system.

* * * * *